US008685227B2

(12) United States Patent
List et al.

(10) Patent No.: US 8,685,227 B2
(45) Date of Patent: Apr. 1, 2014

(54) SAMPLE FLUID TESTING DEVICE AND METHOD FOR ANALYZING A SAMPLE FLUID

(75) Inventors: Hans List, Hesseneck-Kailbach (DE); Michael Marquant, Mannheim (DE); Steven N. Roe, San Mateo, CA (US)

(73) Assignee: Roche Diagnostics Operations, Inc., Indianapolis, IN (US)

( * ) Notice: Subject to any disclaimer, the term of this patent is extended or adjusted under 35 U.S.C. 154(b) by 1306 days.

(21) Appl. No.: 12/257,960

(22) Filed: Oct. 24, 2008

(65) Prior Publication Data

US 2009/0095641 A1 Apr. 16, 2009

Related U.S. Application Data

(63) Continuation of application No. PCT/EP2007/054213, filed on Apr. 30, 2007.

(60) Provisional application No. 60/746,094, filed on May 1, 2006.

(51) Int. Cl.
*G01N 27/327* (2006.01)

(52) U.S. Cl.
USPC ...... 205/775; 204/400; 204/403.03; 205/792; 422/68.1

(58) Field of Classification Search
USPC ........... 204/400, 407; 205/775, 792; 422/68.1
See application file for complete search history.

(56) References Cited

U.S. PATENT DOCUMENTS

| 5,282,950 | A | 2/1994 | Dietze et al. |
| 5,395,504 | A | 3/1995 | Saurer et al. |
| 2002/0057993 | A1* | 5/2002 | Maisey et al. ............. 422/82.01 |
| 2005/0019953 | A1* | 1/2005 | Groll ........................ 436/514 |
| 2005/0145491 | A1* | 7/2005 | Amano et al. ........... 204/403.02 |
| 2005/0230253 | A1 | 10/2005 | Marquant |

(Continued)

FOREIGN PATENT DOCUMENTS

| EP | 0 373 629 A1 | 6/1990 |
| EP | 0 523 463 A2 | 1/1993 |

(Continued)

OTHER PUBLICATIONS

International Patent Application PCT/EP2007/054213 International Search Report mailed Aug. 27, 2007.

*Primary Examiner* — Keith Hendricks
*Assistant Examiner* — Kourtney S Carlson
(74) *Attorney, Agent, or Firm* — Woodard, Emhardt, Moriarty, McNett & Henry LLP

(57) ABSTRACT

The invention refers to a sample fluid testing device for analyzing a sample fluid, comprising a test media tape (1) comprising a tape (2) and a plurality of test media portions (3), each test media portion (3) containing a sensor field (7) for producing electrical signals, when the sample fluid is applied and at least two electrodes (4), the at least two electrodes (4) being positioned in the sensor field (7) and being electrically connected to at least two contact fields (5). The sample fluid testing device contains at least one roller with a surface (17), which contains at least one contact zone (14), the at least one roller (12, 13) being in rolling engagement with the test media tape (1) with its surface (17) in order to successively electrically contact the test media portions (3) via at least one contact field (5) with the at least one contact zone (14), the at least one contact zone (14) on the at least one roller (12, 13) being electrically connected to a meter for measuring the electrical signals.

27 Claims, 2 Drawing Sheets

(56) References Cited

FOREIGN PATENT DOCUMENTS

| | | |
|---|---|---|
| EP | 1 424 040 A1 | 6/2004 |
| JP | H06-222035 A | 8/1994 |
| JP | H04-042047 | 2/1999 |
| JP | 2002-310972 A | 10/2002 |
| JP | 2003-083927 A | 3/2003 |
| WO | WO 99/09621 A1 | 2/1999 |
| WO | WO 01/23885 A1 | 4/2001 |
| WO | WO 01/73109 A2 | 10/2001 |
| WO | WO 2004/030822 A1 | 4/2004 |
| WO | WO 2004/056269 A1 | 7/2004 |
| WO | WO 2005/047861 A2 | 5/2005 |
| WO | WO 2005080966 A1 * | 9/2005 |

* cited by examiner

SAMPLE FLUID TESTING DEVICE AND METHOD FOR ANALYZING A SAMPLE FLUID

CROSS REFERENCE TO RELATED APPLICATIONS

This application is a continuation of International Application No. PCT/EP2007/054213, filed Apr. 30, 2007, which claims the benefit of U.S. Provisional Application No. 60/746,094, filed May 1, 2006, both of which are hereby incorporated by reference in their entirety.

BACKGROUND

The present invention refers to a sample fluid testing device and a method for analyzing a sample fluid, using a test media tape.

Sample fluid testing devices are used e.g. by diabetics for regularly testing samples of their blood to determine the level of blood glucose. In one known type of fluid testing devices, disposable test strips are used to test the sample fluid, each test strip comprising a sensor field, which contains a reagent material that will react with an analyte within the sample fluid. One possibility well-known in the art for analyzing the sample fluid on the sensor field is an electrochemical analysis. For the electrochemical analysis, electrical signals produced within the sensor field which contains the sample fluid are relayed from electrodes within the sensor field to a meter via electrically conductive tracks, the meter being part of the sample fluid testing device. After the measurement has been taken, the test strip is disposed of.

Other known types of fluid testing devices contain test media cassettes with a plurality of sensor fields on a test media tape, the test media tape being provided on a reel within the test media cassette.

WO 2004/056269 A1 is directed towards a body fluid testing device for analyzing a body fluid, comprising: a test media tape adapted to collect the body fluid, said test media tape comprising a tape and test media portions, wherein a free tape portion without test medium is located between successive test media portions. The testing device further comprises a supply portion, which comprises a housing in which an uncontaminated test media tape is contained, the housing further having an opening for withdrawing the test media tape from the housing. The supply portion further has a sealing means for closing the opening against the surrounding. A free tape portion of the test media tape is located between a surface (typically a wall of the housing) and the sealing means when the sealing means closes the opening.

EP 1 424 040 A1 relates to a body fluid testing device for analyzing a body fluid, comprising: a test media tape adapted to collect the body fluid, a supply portion storing an uncontaminated section of the test media tape, a storage portion for storing a contaminated section of the test media tape, an exposure portion positioned between the supply portion and the storage portion, the exposure portion being adapted to expose a section of the test media tape to the body fluid. The exposure portion has a tip portion for exposing a test medium to body fluid application.

For electrochemically analyzing a sample fluid on such a test media tape, an electrical contact from a meter within the sample fluid testing device to the sensor fields on the test media tape has to be established. One known solution for establishing this contact is e.g. described in WO 01/23885 A1. This document refers to a test device for testing of analyte concentration in a fluid to be applied thereto, the device comprising a plurality of sensors on a reel, each of the sensors carrying reagent means for producing an electrical signal in response to the concentration of analyte in an applied fluid. Each of these sensors has a plurality of electrodes, corresponding electrodes of adjacent sensors being connected together by a conductive track on the reel. The device further comprises a meter with electronic means for producing a signal output which is dependent on the electrical signal from the sensors. The meter has contacts, which are electrically connected with the conductive tracks. In this test device, all the sensors are connected by the conductive track, the meter also being permanently connected to the conductive track. The application of a sample fluid to any of the sensors will produce an electrical signal, which is detectable by the meter. A used sensor can be separated from the end of the reel, before a subsequent measurement is taken in order to prevent the generation of electrical signals by the used sensor during the subsequent measurement.

Another example for a sample fluid testing device with such a solution for the electrical contact between the sensor fields and the meter is described in US 2005/0230253 A1.

One disadvantage of this solution is that the long conductive track connecting the electrodes of adjacent sensors has a high resistance, which above all is altered, when the individual sensors are separated from the reel. Furthermore, the unused sensors are not totally passive and can produce interfering signals, which are not related to the analyzed sample fluid. Moreover, the separated sensors are contaminated with the sample fluid and have to be safely discarded, whereas a continuous test media tape, from which the used sensors are not separated, could be stored conveniently on a reel within a waste portion of the test media cassette.

U.S. Pat. No. 5,395,504 A therefore proposes a test media tape with a plurality of separately arranged sensors, which are contacted successively. The contact of each sensor with an electronic circuit is provided by means of resilient foils coming into contact with zones of contact of the sensor by means of a slide connection. One drawback of a slide connection is, that the sliding of the slide contacts over the surface of the moving test media tape when the next sensor is to be used can damage the elements on the surface of the test media tape, e.g. electrodes or conductive tracks made of very thin metal layers (approximately 50 nm).

WO 2005/047861 A2 discloses a biochemical analysis instrument for multiple fluid analysis including a housing, a sensor for sensing a reaction disposed in the housing, an aperture formed in the housing and a test tape housing area formed in the housing. The sensor is disposed to selectively move within the housing area, the aperture being formed to provide access to this tape housing area. The instrument further includes a cassette configured to be received within the tape housing area. The cassette includes a case, a first chamber formed in the case, a second chamber formed in the case, a gap formed in the case, wherein the first chamber and the second chamber are disposed at a respective side of the gap. A test tape is disposed within the housing, which extends from the first chamber across the gap to the second chamber, the test tape having a plurality of active zones disposed at predetermined spaced intervals along the tape for testing an analyte. An electrode based sensor head can be moved forward to contact the test tape and retracted into its original lower non-contact position. Such a solution for contacting the sensors requires a complex construction of the sample fluid testing device to enable the movement of the sensor head and the test tape and to detect their relative positions.

SUMMARY

The present invention is therefore based on the object of avoiding the disadvantages of the prior art and especially of presenting a sample fluid testing device, which allows a safe and easy establishment of an electrical contact of a meter with the electrodes within a sensor field on a test media tape.

These objects are achieved by a sample fluid testing device for analyzing a sample fluid, comprising a test media tape comprising a tape and plurality of test media portions. Each test media portion contains a sensor field for producing electrical signals when the sample fluid is applied. The test media portions further contain at least two electrodes, the at least two electrodes being positioned in the sensor field and being electrically connected to at least two contact fields on the test media portion. The sample fluid testing device further comprises at least one roller with a surface which contains at least one contact zone. The at least one roller is in rolling engagement with the test media tape with its surface in order to successively electrically contact the test media portions via at least one contact field with the at least one contact zone. The at least one contact zone on the at least one roller is electrically connected to a meter for measuring the electrical signals.

The sample fluid testing device can be provided for analyzing sample fluids selected from the group of body fluids, environmental samples, food samples or the like. Preferably, the sample fluid testing device according to the invention determines the concentration of glucose in blood samples.

The sample fluid testing device comprises a test media tape. This test media tape contains a tape, which is an elongate band used as a carrier for the test media portions. Preferably, the tape is made of an electrically insulating, non hygroscopic material, e.g. plastic foils from polyester, polycarbonate, cellulose derivatives and polystyrene. The test media portions of the test media tape are separate testing elements, which are arranged successively and preferably spaced to one another on the tape. They can be produced in the form of labels, which are fixed to the tape by an adhesive layer. Preferably, a free tape portion is located between successive test media portions of the test media tape. The test media portions each contain a sensor field, which may contain a reagent material and in which the sample fluid is analyzed electrochemically. For this purpose, each sensor field contains at least two electrodes. The at least two electrodes are electrically connected to at least two contact fields, which are also arranged on the test media portion. The contact fields are provided for electrically contacting the electrodes of the sensor field with connecting elements of a meter for measuring electrical signals produced in the sensor field. According to the present invention, the sample fluid testing device comprises at least one roller for establishing the electrical contact between the contact fields and the meter. The surface of this roller (which is preferably cylindrical) contains at least one (electrically conducting) contact zone. This contact zone is preferably surrounded by insulating material on the surface of the roller. The at least one roller is in rolling engagement with the test media tape with its surface. Preferably, the roller rolls along the surface of the test media tape in a longitudinal direction when the test media tape is moved to its next testing position, in which the sample fluid can be applied to the next media portion, while the roller does not change its position within the sample fluid testing device. The roller is arranged to electrically contact successively the test media portions via their contact fields, when the at least one contact zone of the roller meets a contact field on the test media tape surface. By establishing this contact, electrical signals produced in the sensor field can be conducted from the electrodes via the contact field and the contact zone to a meter for measuring these signals, the contact zone of the roller being electrically connected to the meter. The meter preferably contains means for evaluating the measured electrical signals, e.g. to determine the concentration of an analyte within the sample fluid, and means for displaying an analysis result to the user of the sample fluid testing device.

The present invention further refers to a method for analyzing a sample fluid, wherein the sample fluid is analyzed on a test media tape, the test media tape comprising a plurality of test media portions, each test media portion containing a sensor field for producing electrical signals when the sample fluid is applied and at least two electrodes. The at least two electrodes are positioned in the sensor field and are electrically connected to at least one contact field of the test media portion. The method comprises the steps of applying a sample fluid to the sensor field of a test media portion and of rolling at least one roller with a surface, which contains at least one contact zone, along the test media tape, in order to electrically contact the contact fields of the test media portion with the at least one contact zone. Furthermore, it comprises measuring the electrical signal produced within the sensor field with a meter, which is electrically connected to the at least one contact zone of the roller. This method is preferably carried out using a sample fluid testing device according to the present invention. The analyzed sample fluid is preferably selected from the group of body fluid, environmental sample and food sample. The order of applying the sample fluid and electrically contacting the contact fields by means of the roller can be freely chosen.

The present invention further refers to a method for preparing a sample fluid testing device for analyzing a sample fluid, wherein the sample fluid is analyzed on a test media tape, the test media tape comprising a plurality of test media portions, each test media portion containing a sensor field for producing electrical signals, when the sample fluid is applied, and at least two electrodes, the at least two electrodes being positioned in the sensor field and being electrically connected to at least two contact fields of the test media portion. According to this method, at least one roller is rolled with its surface, which contains at least one contact zone, along the test media tape, in order to electrically contact the contact fields of the test media portion with the at least one contact zone, which is electrically connected to a meter. When this contact is established, the sample fluid testing device is prepared to analyze a sample fluid electrochemically in the sensor field of the contacted test media portion.

One advantage of the device and the method according to the present invention is, that an electrical contact between a meter and an individual test media portion of a test media tape can be established without scratching over the surface of the test media tape and without a complicated mechanism for placing an electrical contact element exactly on the contact fields of the test media portion.

According to a preferred embodiment of the present invention, the at least one contact zone of the at least one roller is electrically connected to the meter by a sliding contact. Thereby, the functions of contacting the contact fields on the movable test media tape and of connecting the rotatable roller to the immobile meter are separated.

According to a preferred embodiment of the present invention, the at least one contact zone is an electrically conducting annular zone arranged on the circumference of the surface of the roller. Such a roller can be produced by stacking alternately round discs of a conducting material and round discs of an insulating material and joining them to form a cylindrical roller. The round discs of conducting material will then form annular contact zones on the surface of the roller, flanked by annular non conducting zones formed by the discs of insulating material. The contact zones of the roller can also be produced by coating selected zones (e.g. annular zones) on the surface of a roller with a conducting material (e.g. a metal), the roller consisting of an insulating material.

In the sample fluid testing device according to the invention, the contact fields can be arranged in at least two rows on the test media portion, the rows being arranged in a transverse direction of the test media tape and the contact fields within two different rows being shifted to one another in the transverse direction. This arrangement is especially favourable if a plurality of contact fields is required for each test media portion. In this case, the contact fields would have to be very narrow if they were all placed side by side on the test media tape, making their production and contacting difficult. By placing the contact fields in rows and shifted to one another, this problem can be overcome. The contact fields in the at least two rows can be contacted by one roller, which is in rolling engagement successively with the each row of contact fields. The contact fields in the at least two rows can also be contacted by at least two rollers, which are arranged next to each other and which can be in rolling engagement at the same time with at least two rows of contact fields.

Preferably, at least one counter roll is arranged on one side of the test media tape for producing a contact pressure of the test media tape against the at least one roller on the other side of the test media tape. This can be an elastic roll or a roll being pressed by an elastic element (e.g. a spring) against the other side of the test media tape.

According to a preferred embodiment of the present invention, the test media tape is housed in a cassette. The cassette is used for storing the test media tape within the sample fluid testing device. After all test media tape portions of one cassette are used up, preferably a new test media cassette with uncontaminated test media portions on a test media tape can be inserted into the sample fluid testing device. The unused and/or the used test media tape can be stored within the cassette on a reel.

Preferably, the cassette comprises a supply portion for storing unused test media tape, the supply portion having a port for withdrawing test media tape from the supply portion and said supply portion further having sealing means for closing the port in a first position of the sealing means and for opening the port in a second position of the sealing means. The sealing means is provided for preventing the entry of humidity and/or contaminants into the supply portion of the cassette. The port, by which the test media tape can be withdrawn, can be opened and closed by the sealing means. Preferably, it is opened, when the test media tape is moved, in order not to damage any components of the test media tape, e.g. the sensor field or thin conducting metal layers, by squeezing it through the sealing means. The opening and closing can be effected automatically or manually. The automatic operation of the sealing means can include, for example, the use of hydraulic means.

Preferably, the automatic operation of the sealing means is coupled to a position identification means, the port being opened by the sealing means when the position identification means identifies a first position of the test media tape within the sample fluid testing device and the sealing means closing the port when the position identification means identifies a second position. Preferably, the port is closed by the sealing means only when the sealing means is positioned at a free tape portion of the test media tape. The position identification means can be coupled to at least one of the contact zones on the roller. When this contact zone contacts a contact field on the test media tape, which can be provided especially for this function, a certain position of the test media tape is identified. According to a preferred embodiment of the present invention, the test media tape is advanced by a drive means, rolling the roller passively or actively along the test media tape, the drive means advancing the test media tape until the at least one contact zone of at least one roller electrically contacts certain contact fields of a test media portion.

According to a preferred embodiment of the present invention, a cassette with a supply portion for storing unused test media tape further comprises a waste portion for receiving a test media tape that is contaminated with the sample fluid.

BRIEF DESCRIPTION OF THE DRAWINGS

The present invention is explained in greater detail below with reference to the drawings.

DESCRIPTION OF THE SELECTED EMBODIMENTS

Figure 1:
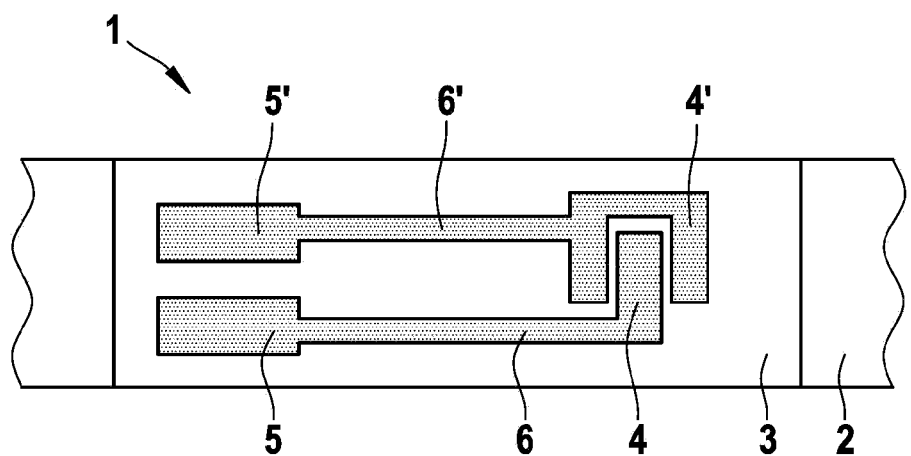
FIG. 1 shows schematically a section of a first test media tape, which can be used for the present invention.

In FIG. 1, a section of a test media tape with a test media portion having two electrodes and two contact fields is shown.

The test media tape 1 comprises a tape 2 and a test media portion 3. The test media portion 3 contains two electrodes 4 and 4', which are positioned in a sensor field (not shown). The two electrodes 4 and 4' are electrically connected (via conductors 6 and 6') to two contact fields 5 and 5', which are to be electrically contacted by means of a roller (not shown) within a fluid testing device according to the present invention. The test media tape has a plurality of sections as shown in FIG. 1.

Figure 2:
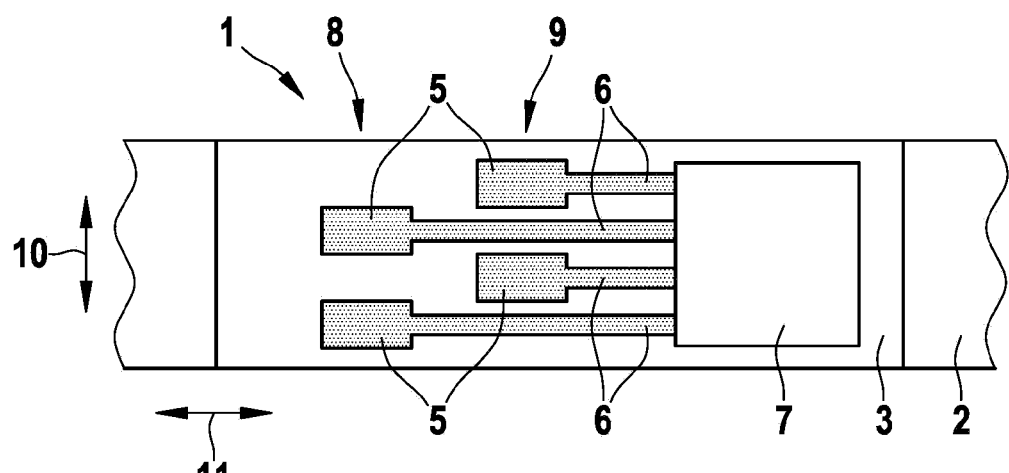
FIG. 2 shows schematically a section of a second test media tape, which can be used for the present invention

In FIG. 2, a section of another test media tape with a test media portion having a sensor field and four contact fields is shown.

The test media tape 1 comprises a tape 2 and a test media portion 3. The test media portion 3 contains a sensor field 7, in which electrodes (not shown) are arranged. The electrodes are connected via conductors 6 to four contact fields 5, which are arranged two by two in a first row 8 and a second row 9, the rows 8, 9 being arranged in a transverse direction 10 of the test media tape 1. The contact fields within the two rows 8, 9 are shifted to one another in the transverse direction 10, so that they do not lie in one line in the longitudinal direction 11 of the test media tape 1. A test media tape 1 to be used in a sample fluid testing device according to the present invention comprises a plurality of sections as shown in FIG. 2.

Figure 3:
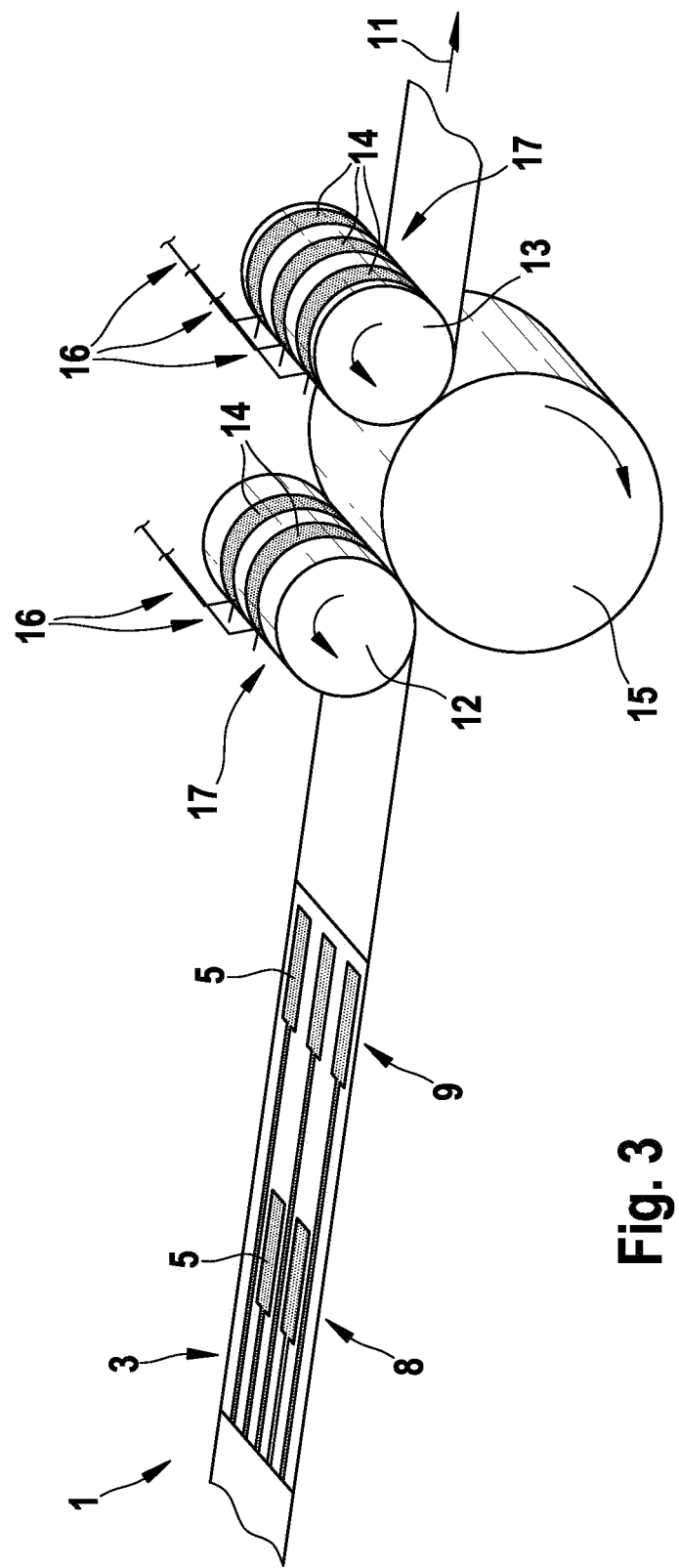
FIG. 3 shows schematically two rollers in rolling engagement with a test media tape in a sample fluid testing device according to the present invention.

In FIG. 3, two rollers of a sample fluid testing device according to the present invention are shown in rolling engagement with a test media tape.

The test media tape 1 comprising a plurality of test media portions 3 (only one shown in FIG. 3) is movable within the sample fluid testing device in the longitudinal direction 11. Each test media portion 3 comprises (in this case) five contact fields 5, which are arranged in two rows 8, 9 and which are to be electrically contacted. Two rollers 12, 13 are provided for contacting the contact fields 5. The first roller 12 contains two annular contact zones 14 and the second roller 13 contains three annular contact zones 14 on the surface 17. Both rollers 12, 13 are in rolling engagement with the test media tape 1. An elastic roll 15 is arranged on the side of the test media tape 1 opposite the side with the rollers 12, 13 to produce a contact pressure of the test media tape 1 against the rollers 12, 13. When the test media tape 1 is moved in the longitudinal direction 11, the rollers 12, 13 and the elastic roll 15 roll along the two surfaces of the test media tape 1 in different rotating directions. When the rollers 12, 13 reach a test media portion 3, the first roller 12 electrically contacts the two contact fields 5 in the first row 8 with its two contact zones 14 and the second roller 13 electrically contacts the three contact fields 5 in the second row 9 with its three contact zones 14. The contact zones 14 of both rollers 12, 13 are electrically connected to a meter (not shown) by sliding contacts 16.

REFERENCE NUMBERS

1 test media tape
2 tape
3 test media portion
4, 4' electrodes
5, 5' contact fields
6, 6' conductors
7 sensor field
8 first row
9 second row
10 transverse direction
11 longitudinal direction
12 first roller
13 second roller
14 contact zones
15 elastic roll
16 sliding contacts
17 surface

The invention claimed is:

1. A sample fluid testing device for analyzing a sample fluid, comprising a test media tape comprising a tape and a plurality of test media portions, each test media portion containing a sensor field for producing electrical signals when the sample fluid is applied and at least two electrodes, the at least two electrodes being positioned in the sensor field and being electrically connected to at least two contact fields on the test media portion, the sample fluid testing device having at least one roller with a surface, which contains at least one contact zone, the at least one roller being in rolling engagement with the test media tape with its surface in order to successively electrically contact the test media portions via at least one contact field with the at least one contact zone, the at least one contact zone on the at least one roller being electrically connected to a meter for measuring the electrical signals, wherein the at least one contact zone is an electrically conducting annular zone arranged on the circumference of the surface of the roller, wherein the contact zone is flanked by insulating material on the at least one roller.

2. The sample fluid testing device according to claim 1, wherein at least one contact zone of the at least one roller is electrically connected to the meter by a sliding contact.

3. The sample fluid testing device according to claim 1, wherein the contact fields are arranged in at least two rows, the rows being arranged in a transverse direction of the test media tape and the contact fields within two different rows being shifted to one another in the transverse direction.

4. The sample fluid testing device according to claim 1, wherein at least one counter roll is arranged on one side of the test media tape for producing a contact pressure of the test media tape against at least one roller on the other side of the test media tape.

5. The sample fluid testing device according to claim 1, wherein the test media tape is housed in a cassette.

6. The sample fluid testing device according to claim 5, wherein the cassette comprises a supply portion for storing unused test media tape, the supply portion having a port for withdrawing test media tape from the supply portion and said supply portion further having sealing means for closing said port in a first position of the sealing means and for opening said port in a second position of the sealing means.

7. The sample fluid testing device according to claim 6, wherein the cassette comprises a waste portion for receiving test media tape that is contaminated with the sample fluid.

8. A method for analyzing a sample fluid, wherein the sample fluid is analyzed on a test media tape, the test media tape comprising a plurality of test media portions, each test media portion containing a sensor field for producing electrical signals when the sample fluid is applied and at least two electrodes, the at least two electrodes being positioned in the sensor field and being electrically connected to at least two contact fields of the test media portion, the method comprising applying a sample fluid to the test field of a test media portion and rolling at least one roller with a surface, which contains at least one contact zone, along the test media tape, in order to electrically contact the contact fields of the test media portion with the at least one contact zone and measuring the electrical signals produced within the sensor field with a meter, which is electrically connected to the at least one contact zone of the roller, wherein the at least one contact zone is an electrically conducting annular zone arranged on the circumference of the surface of the roller, wherein the contact zone is flanked by insulating material on the at least one roller.

9. The method according to claim 8, wherein the test media tape is advanced by a drive means, rolling the roller along the test media tape, the drive means advancing the test media tape until the at least one contact zone of the at least one roller electrically contacts certain contact fields on a test media portion.

10. The method according to claim 8, further comprising:
   wherein the at least one roller includes a first roller and a second roller;
   wherein the contact fields are arranged in at least two rows, the rows being arranged in a transverse direction of the test media tape and the contact fields within two different rows being shifted to one another in the transverse direction; and
   wherein said rolling includes electrically connecting the first roller to one of the rows of the contact fields and the second roller to the other row of the contact fields.

11. The method according to claim 8, further comprising: producing a contact pressure of the test media tape with at least one counter roll arranged on one side of the test media tape against the at least one roller on the other side of the test media tape.

12. A sample fluid testing device, comprising:
   a test media tape including a plurality of test media portions, each of the test media portions including
      a sensor field for producing an electrical signal when a sample fluid is applied to the sensor filed, and
      a contact field electrically connected to the sensor field; and
   at least one roller having a surface and an annular contact zone located on the circumference of the surface of the roller, wherein the contact zone is flanked by insulating material on the roller, the roller being in rolling engagement with the test media tape where the contact zone electrically connects the contact field to a meter for measuring the electrical signal from the sensor field.

13. The sample fluid testing device according to claim 12, wherein the contact zone of the roller is electrically connected to the meter by a sliding contact.

14. The sample fluid testing device according to claim 12, further comprising:

the contact field being incorporated into a first row of contact fields;

the test media tape including a second row of contact fields electrically connected to the sensor field, wherein the contact fields in the second row are shifted in a transverse direction relative to the first row of contact fields; and a second roller having contact zones positioned to contact the second row of contact fields.

15. The sample fluid testing device according to claim 12, wherein at least one counter roll is arranged on one side of the test media tape for producing a contact pressure of the test media tape against the roller on the other side of the test media tape.

16. The sample fluid testing device according to claim 12, wherein the test media tape is housed in a cassette.

17. A method for analyzing a sample fluid, comprising:
advancing a test media tape with at least one roller rolling against the test media tape, wherein the roller has an annular contact zone disposed on the circumference of a surface of the roller, wherein the contact zone is flanked by insulating material on the roller, wherein the test media tape has a sensor field and a contact field electrically connected to the sensor field;

establishing an electrical connection between a meter and the sensor field by rolling the contact zone on the roller into contact with the contact field of the test media tape; and measuring electrical signals produced from the sensor field with the meter when the sample fluid is applied to the sensor field.

18. The method according to claim 17, further comprising:
wherein the contact field is incorporated into a first row of contact fields on the test media tape;
wherein the test media tape includes a second row of contact fields electrically connected to the sensor field, wherein the contact fields in the second row are shifted in a transverse direction relative to the first row of contact fields;
rolling a second roller against the test media tape, wherein the second roller has a contact zone located directly on the surface of the second roller; and
wherein said establishing electrical the electrical connection includes
contacting the contact zone on the roller with the first row of contact fields, and
contacting the contact zone of the second roller with the second row of contact fields.

19. The method according to claim 17, further comprising:
producing a contact pressure of the test media tape with a counter roll arranged on one side of the test media tape against the roller on the other side of the test media tape.

20. A sample fluid testing device for analyzing a sample fluid, comprising a test media tape comprising a tape and a plurality of test media portions, each test media portion containing a sensor field for producing electrical signals when the sample fluid is applied and at least two electrodes, the at least two electrodes being positioned in the sensor field and being electrically connected to at least two contact fields on the test media portion, the sample fluid testing device having at least one roller with a surface, which contains at least one contact zone, the at least one roller being in rolling engagement with the test media tape with its surface in order to successively electrically contact the test media portions via at least one contact field with the at least one contact zone, the at least one contact zone on the at least one roller being electrically connected to a meter for measuring the electrical signals, wherein the at least one contact zone is an electrically conducting annular zone arranged on the circumference of the surface of the roller, wherein each test media portion has the contact fields at least arranged in a first row and a second row, and wherein the at least one roller includes a first roller configured to contact the first row of the contact fields and a second roller configured to contact the second row of the contact fields.

21. The sample fluid testing device according to claim 20, wherein the contact fields in the first row and the second row are shifted relative to one another in a transverse direction of the test media tape.

22. A method for analyzing a sample fluid, wherein the sample fluid is analyzed on a test media tape, the test media tape comprising a plurality of test media portions, each test media portion containing a sensor field for producing electrical signals when the sample fluid is applied and at least two electrodes, the at least two electrodes being positioned in the sensor field and being electrically connected to at least two contact fields of the test media portion, the method comprising applying a sample fluid to the test field of a test media portion and rolling at least one roller with a surface, which contains at least one contact zone, along the test media tape, in order to electrically contact the contact fields of the test media portion with the at least one contact zone and measuring the electrical signals produced within the sensor field with a meter, which is electrically connected to the at least one contact zone of the roller, wherein the at least one contact zone is an electrically conducting annular zone arranged on the circumference of the surface of the roller, wherein each test media portion has the contact fields at least arranged in a first row and a second row, wherein the at least one roller includes a first roller and a second roller, and contacting the first roller to the first row of the contact fields and the second roller to the second row of the contact fields.

23. A sample fluid testing device, comprising:
a test media tape including a plurality of test media portions, each of the test media portions including
a sensor field for producing an electrical signal when a sample fluid is applied to the sensor filed, and
a contact field electrically connected to the sensor field;
a roller having a surface and an annular contact zone located on the circumference of the surface of the roller, the roller being in rolling engagement with the test media tape where the contact zone electrically connects the contact field to a meter for measuring the electrical signal from the sensor field, wherein each of the test media portions has a first row and a second row of contact fields; and
wherein the at least one roller includes a first roller configured to contact the first row of the contact fields and a second roller configured to contact the second row of the contact fields.

24. The sample fluid testing device according to claim 23, wherein the contact fields in the first row and the second row are shifted relative to one another in a transverse direction of the test media tape.

25. A method for analyzing a sample fluid, comprising:
advancing a test media tape with a roller rolling against the test media tape, wherein the roller has an annular contact zone disposed on the circumference of a surface of the roller, wherein the test media tape has a sensor field and a contact field electrically connected to the sensor field;

establishing an electrical connection between a meter and the sensor field by rolling the contact zone on the roller into contact with the contact field of the test media tape; and measuring electrical signals produced from the sensor field with the meter when the sample fluid is applied to the sensor field, wherein the contact field is positioned in a first row;

wherein the test media tape includes a second contact field located in a second row; and wherein said establishing the electrical connection includes rolling a second roller into contact with the with the second contact field located in the second row.

26. A method for analyzing a sample fluid, comprising:

advancing a test media tape with a roller rolling against the test media tape, wherein the roller has an annular contact zone disposed on the circumference of a surface of the roller, wherein the test media tape has a sensor field and a contact field electrically connected to the sensor field;

establishing an electrical connection between a meter and the sensor field by rolling the contact zone on the roller into contact with the contact field of the test media tape;

measuring electrical signals produced from the sensor field with the meter when the sample fluid is applied to the sensor field;

wherein the contact field is incorporated into a first row of contact fields on the test media tape;

wherein the test media tape includes a second row of contact fields electrically connected to the sensor field, wherein the contact fields in the second row are shifted in a transverse direction relative to the first row of contact fields;

rolling a second roller against the test media tape, wherein the second roller has a contact zone located directly on the surface of the second roller; and wherein said establishing electrical the electrical connection includes contacting the contact zone on the roller with the first row of contact fields, and contacting the contact zone of the second roller with the second row of contact fields.

27. A method for analyzing a sample fluid, comprising:

advancing a test media tape with a roller rolling against the test media tape, wherein the roller has a contact zone disposed directly on a surface of the roller, wherein the test media tape has a sensor field and a contact field electrically connected to the sensor field;

establishing an electrical connection between a meter and the sensor field by rolling the contact zone on the roller into contact with the contact field of the test media tape;

measuring electrical signals produced from the sensor field with the meter when the sample fluid is applied to the sensor field; and producing a contact pressure of the test media tape with a counter roll arranged on one side of the test media tape against the roller on the other side of the test media tape.

* * * * *

UNITED STATES PATENT AND TRADEMARK OFFICE
CERTIFICATE OF CORRECTION

PATENT NO. : 8,685,227 B2
APPLICATION NO. : 12/257960
DATED : April 1, 2014
INVENTOR(S) : List et al.

It is certified that error appears in the above-identified patent and that said Letters Patent is hereby corrected as shown below:

In the Claims
Col. 12, Claim 26, line 7, replace "electrical the electrical" with --the electrical--

Signed and Sealed this
Twenty-fourth Day of June, 2014

Michelle K. Lee
*Deputy Director of the United States Patent and Trademark Office*